United States Patent [19]
Lehner et al.

[11] Patent Number: 5,788,711
[45] Date of Patent: Aug. 4, 1998

[54] IMPLANTABLE POSITIONING AND FIXING SYSTEM FOR ACTUATOR AND SENSOR IMPLANTS

[75] Inventors: Rolf Lehner, Esslingen; Gerd Müller, Unterschleissheim; Hans Leysieffer, Taufkirchen, all of Germany

[73] Assignee: Implex GmgH Spezialhorgerate, Ismaning, Germany

[21] Appl. No.: 726,495

[22] Filed: Oct. 7, 1996

[30] Foreign Application Priority Data

May 10, 1996 [DE] Germany .................. 196 18 964.0

[51] Int. Cl.$^6$ .................................................. A61B 19/00
[52] U.S. Cl. .................. 606/130; 600/25; 623/10; 128/746
[58] Field of Search .................. 606/130, 109, 606/60, 61; 128/746, 739; 600/25; 623/10

[56] References Cited

U.S. PATENT DOCUMENTS

| | | | |
|---|---|---|---|
| 4,498,461 | 2/1985 | Hakansson | 600/25 |
| 4,601,723 | 7/1986 | McGrew | 623/10 |
| 4,606,329 | 8/1986 | Hough | 600/25 |
| 4,809,694 | 3/1989 | Ferrara . | |
| 5,112,336 | 5/1992 | Krevolin et al. . | |
| 5,196,013 | 3/1993 | Harms et al. | 606/61 |
| 5,320,628 | 6/1994 | Ufkin . | |
| 5,344,422 | 9/1994 | Frigg | 606/61 |
| 5,498,226 | 3/1996 | Lenkauskas | 600/25 |
| 5,558,618 | 9/1996 | Maniglia | 600/25 |

OTHER PUBLICATIONS

Partially implantable hearing aid using piezoelectric ceramic ossicular vibrator, Yanagihara et al, Otolaryngologic clinics of North America, vol. 28, Feb. 1995.

Naoaki Yanagihara, MD, Kiyofumi Gyo MD and Yasuyuki Hinohira, MD, "Partially Implantable Hearing Aid Using Piezoelectric Cermaic Ossicular Vibrator", Otolaryngologic Clinics Of North America, vol. 28, No. 1, Feb. 1995, pp. 85-86.

Anthony J. Maniglia, MD, Wen H. Ko, PhD, Mary Rosenbaum, MA et al "Contactless Semi–Immplatable Electromagnetic Middle Ear Device for the Treatment of Sensorieural Hearing Loss", Otolaryngologic Clinics Of North America, vol. 28, No. 1, Feb. 1995, pp. 121-139.

John M. Frderickson, MD, PhD, James M. Coticchia, MD and Sid Khosla, MD "Ongoing Investigations Into an Implantable Electromagnetic Hearing Aid for Moderate to Sever Sensorineural Hearing Loss" Otolaryngologic Clinics Of North America, vol. 28, No. 1, Feb. 1995, pp. 107-119.

Contactless Semi–Implantable Electromagentic Middle Ear Device for the Treatment of Sensor Neural Hearing Loss.

Ongoing Investigations Into an Implantable Electromagnetic Hearing Aid for Moderate to Severe Sensor Neural Hearing Loss.

Partially Implantable Hearing Aid Using Piezoelectric Cermaic Ossicular Vibrator.

*Primary Examiner*—Robert A. Hafer
*Assistant Examiner*—Justine Yu
*Attorney, Agent, or Firm*—Sixbey, Friedman, Leedom & Ferguson; David S. Safran

[57] ABSTRACT

A permanently implantable, fixable positioning system (1) for stationary attachment to a human body, without play, preferably to the human skull. It has ball-and-socket joint (3), linear axle (4) fixed stationary to it, and a carriage (5) which is guided on the linear axle for accommodating an implantable actuator or sensor device (6). The combination of the axial degree of freedom of the linear axle (4) with three degrees of rotational freedom of the ball-and-socket joint (3) allows a surgeon four-axis, in-situ positioning of the implantable means especially in the middle ear and mastoid cavities. By using the positioning system, precise positioning of a free active end (16) of the implantable device (6) relative to sensitive anatomical structures of the human body is enabled while avoiding risky relative movements between the implantable device and the body of the patient. The positioning system is thus used more or less as a "tremor-free artificial hand" of the surgeon. According to one preferred embodiment, the implantable device is an implantable piezoelectric hearing aid transducer of a partially or completely implantable hearing aid.

12 Claims, 4 Drawing Sheets

IMPLANTABLE POSITIONING AND FIXING SYSTEM FOR ACTUATOR AND SENSOR IMPLANTS

BACKGROUND OF THE INVENTION

1. Field of the Invention

The invention relates to a permanently implantable device for intraoperative positioning and subsequent fixing of an implantable actuator or sensor means (hereinafter abbreviated as "implantable means") in the human body, especially in the mastoid and middle ear region of the skull.

2. Description of Related Art

In view of the extraordinarily small and sensitive anatomical structures in the human body, especially in the mastoid and middle ear region of the skull, it is almost impossible to maintain the position of an implantable means by hand guidance for longer than a few seconds or this requires considerable expenditure of force and concentration by the surgeon. Many interventions in the body, especially in the skull area, however require targeted, fixable positioning of suitable actuator or sensor means over longer time intervals.

Based on the fact that hand-guided actuator or sensor means for microsurgical, therapeutic or diagnostic manipulations on sensitive small structures, for example, of the skull, always entail risk, that due to possible relative movements between hand-guided means and the body of the patient these target structures are damaged or altered under certain circumstances, in this technology there has long been a desire to have a positioning system which can be anchored in a fixed position relative to the body, especially to the skull, by means of a holder.

Three implantable actuator holders are known from the prior art. A first holder, as a component of a partially implantable piezoelectric hearing aid concept for stimulation of the stapes, was described by N. Yanagihara, K. Gyo and Y. Hinohira in the article "Partially Implantable Hearing Aid Using Piezoelectric Ceramic Ossicular Vibrator" which appeared in The Otolaryngolic Clinics of North America-Electronic Implantable Hearing Devices for Partial Hearing Loss, 1995, W. B. Saunders Company. The external part of the device is made like a conventional hearing aid which is worn behind the ear and contains a microphone, amplifier, battery and external transmitting coil. The internal part of the device which is fixed on the skull cap is used to hold the receiving coil. There is a relatively simple L-shaped attachment element anchored to the bone for positioning and fixing of the piezoelectric bimorph transducer in the middle ear. It is a retaining plate which can be fixed on the skull cap using two bone screws and which is composed of a metal plate with two longitudinal holes and a wire axle attached vertically thereto. After screwing the metal plate onto the skull cap, the wire axle points to the middle ear (medially). On the wire axle, a sleeve can be axially moved, and thus, the piezoelectric bimorph transducer attached in turn to the sleeve can be positioned. This enables an axial and rotational degree of freedom on the wire axle. After removing the malleus and incus, the free end of the piezoelement can be attached, preferably, directly to the head of the stapes with cyanoacrylate adhesive.

A second retaining system for an actuator implant module which improves hearing was described by J. Frederickson, J. M. Coticchia and S. Khosla in the article entitled "Ongoing Investigation into an Implantable Electromagnetic Hearing Aid for Moderate to Severe Sensorineural Hearing Loss" which appeared likewise in The Otolaryngolic Clinics of North America-Electronic Implantable Hearing Devices for Partial Hearing Loss, 1995, W. B. Saunders Company. In this case, the retainer is a component of a partially implantable electromagnetic hearing aid which, to date, has only been tested in an animal model, and which, for implantation, has a small hole made with a surgical laser in the body of incus for attachment of a permanent magnet. In doing so, the laser head is guided in a mounting ring with internal and external threads which is screwed into the mastoid bone and whose longitudinal axis points toward the body of incus. After making the laser hole in the incus and removing the laser head, the electromagnetic drive (transducer probe tip) can be screwed into this mounting ring and positioned medially relative to the magnet on the ossicle.

A third retaining system was developed by Maniglia et al. for a partially implantable electromagnetic middle ear stimulator [A. J. Maniglia, W. H. Ko, M. Rosenbaum, T. Falk, W. L. Zhu, N. W. Frenz, J. Werning, J. Masin, A. Stein and A. Sabri, "Contactless Semi-Implantable Electromagnetic Middle Ear Device for the Treatment of Sensorineural Hearing Loss", which appeared in The Otolaryngolic Clinics of North America-Electronic Implantable Hearing Devices for Partial Hearing Loss, 1995, W. B. Saunders Company]. Here, a small magnet is cemented to the incus using dental cement. Along a titanium guide shaft which can be implanted in the mastoid, the drive coil can be positioned except for an air gap of a maximum 1 mm relative to the permanent magnet on the ossicle. This titanium shaft, as in the Yanagihara et al. version, has two longitudinal holes and an additional drill hole for fixing on the skull cap by means of three bone screws. By means of a threaded axle, an electronic module and the drive coil attached to it can be positioned medially in a longitudinal hole guide and fixed on the shaft via a screw with a locknut.

All three retaining systems known from the prior art are used for permanent fixing of components of hearing aids to the skull bone or in the vicinity of the middle and inner ear. They are characterized, overall, by an extremely limited intraoperative positioning capacity due to the lack of usable degrees of freedom, and overall, they must be adapted to the anatomical circumstances of the implantation site and to the previously established location of the destination in the middle ear by more or less precise manual bending into shape. The first and the third of these retaining systems, moreover, require adhesive or surgical cement for fixing the component and are often unsuitable as long term implants due to strength losses.

Thus, in many regards there is a need for a device which can be permanently attached to the human skull without adhesives or surgical cements in order to position surgical, therapeutic or diagnostic sensors or actuators in the body free of relative movements and to fix them in the ascertained position.

SUMMARY OF THE INVENTION

The primary object of the present invention is to avoid the disadvantages known from the prior art, i.e., to increase the overly small number of degrees of freedom and thus to avoid manual bending of the implant holder to shape.

In conjunction with the preceding object, it is also an object to make possible a permanently secured fixation in a three-dimensional location of the positioned implantable means with respect to the destination on the body, in order to reliably prevent any risky change of the position of the sensor/actuator after completed implantation.

This object is achieved by a permanently implantable, fixable positioning system for the stationary attachment to the human body, without play, especially to the human skull, with:

a ball-and-socket joint which can be fixed by a clamp mechanism and which can be manually positioned with an auxiliary tool, a linear axle which is joined stationary to the ball of the ball-and-socket joint, a carriage which is guided in a guide of the linear axle and which can be manually positioned using an auxiliary tool, via a threaded drive, freely between end stops of the linear axle, and a receiver attached to the carriage for an actuator or sensor means to be positioned or fixed.

The positioning system to be affixed to the body is used with its receiver for any actuator, sensor, mechanical or optical means as an "artificial, steady hand" of the surgeon to position and then fix the free active end of the implantable means relative to a destination on the body without significant risky relative movements occurring in doing so.

In particular, the linear axle can be made self-locking so that, using a structure as simple as possible, automatic displacement of the carriage with the implantable means attached thereto is prevented.

A threaded spindle for axial and self-locking carriage movement which has a receiver for an auxiliary tool, for example, a screwdriver, can be provided.

Furthermore, the clamp mechanism can have two plates between which the ball-and-socket joint can be fixed by clamping using attachment screws. Thus, three degrees of rotational freedom of the actuator or sensor means can be easily fixed.

Advantageously, the positioning system is designed such that only a single auxiliary tool, for example, an Allen wrench, is necessary, when the ball-and-socket joint is unclamped for adjustment of all three degrees of rotational freedom of it. It is a further advantage that the positioning system is also designed such that the instantaneous position of the three degrees of rotational freedom is maintained even when the ball-and-socket joint is unclamped, being secured by frictional forces, and is permanently maintained after closing the clamp.

To facilitate insertion and adjustment of the positioning system for the surgeon, the controls for manual positioning of the ball-and-socket joint and the carriage and for clamping the ball-and-socket joint, preferably, point away from the body of the patient toward the surgeon. In this respect, moreover, it is advantageous if the construction and the geometrical dimensions of the positioning system are such that the surgeon, with the naked eye or using a microscope, always maintains an unobstructed view of at least the free active end of the actuator or sensor means and of the implantation area together with the destination in the body of the patient. In this way, the risks to the patient otherwise caused by possible faulty positioning of the implantable means are kept especially low.

To attach the positioning system, especially to the surface of a cranial bone, preferably, there are openings into which bone screws can be inserted and screwed to the cranial bone. Thus, for permanent fixing of the device to the body, and of the implantable means in the device, no adhesives or bone cements are necessary at all.

Relative movements between the partially microscopically small target structures located in the body and the implantable means attached in the positioning system are minimized by screwing the positioning system to the skull. When unclamped, controlled and low-risk positioning of the implantable means and its active end is thus possible relative to the destinations on the body.

According to one especially preferred embodiment the positioning system according to the invention is a manually operated positioning system which can be locked in its rotational degrees of freedom and which has the following components:

a head plate which can be permanently fixed on the cranial bone by means of special bone screws, a clampable ball-and-socket joint which is attached to the head plate, and is movable in all three degrees of rotational freedom, a linear axle which is fixedly joined to the ball of the ball-and-socket joint, a carriage which is guided on the linear axle and which can be freely positioned axially via a precision threaded drive between the two end stops of the linear axle, a receiver located on the carriage for the implantable means to be positioned, and a clamp mechanism which permanently fixes the intra-operatively set position of all degrees of rotational freedom including the location of the implantable means in the carriage.

A number of advantages are achieved by the clampable positioning system which is proposed by the present invention, especially by the preferred embodiments described below. There is a simple, compact structure of relatively few components which, themselves, in turn, can be easily designed and built. In proper use, this also ensures a high degree of hardware safety for users, patients and third parties. External influences such as, for example, vibrations and changes of temperature, location and pressure cannot adversely affect system function.

For example, the mastoid antrum, which is under the external ear (pinna) in the cranial bone, is considered the preferred region of the body into which the positioning system together with the implantable means can be placed. It can be opened using standard microsurgical techniques. Its volume is then several cubic centimeters and is subject to three-dimensional model variation which is specific to the patient.

The head plate of the positioning system, in this case, is screwed onto the surface of the cranial bone which immediately adjoins the edge of the formed mastoid antrum. The system is designed such that it does not protruse above the level of the calvarial arch. This ensures that the implanted system does not show under the skin after the operation.

In this way, tremor-free intraoperative positioning and fixing of any implantable means, for example, on one of the three ossicles of the ossicular chain (malleus, incus, stapes), the bony separating wall between the air-filled middle ear and liquid-filled inner ear (promontorium), in the liquid-filled inner ear itself, and the bordering vestibular organ is possible. Other applications of the system according to the invention include short-term, intraoperative laser surgery in the entire cranial area including microcoagulation or tissue obliteration. When a measurement laser is coupled, vibrations, for example, of the ossicular chain, the eardrum or the round window membrane can be measured intraoperatively without contact.

In one preferred embodiment of the invention, the above described implantable positioning system is combined with an actuator hearing aid transducer which is used for vibrational stimulation of the hard-of-hearing to improve hearing. This preferred embodiment is thus a component of a partially or completely implantable hearing aid.

In this case the head plate of the positioning and fixing system is permanently fixed to the cranial bone by means of special bone screws, in the receiver of the carriage a piezoelectric hearing aid transducer which stimulates the ossicle is attached, the positioning system together with the hearing aid transducer attached to it in the surgically milled-out mastoid antrum in the cranial bone has room under the external ear, without postoperative protrusion through the covering skin, the hearing aid transducer is located in the receiver of the carriage such that its free active end points into the body interior, preferably into the spaces of the middle ear toward one of the ossicles in the body (malleus, incus, stapes), the free active end of the hearing aid transducer can be positioned at a selected destination of the ossicular chain and can be seated there, the system is designed such that different destinations of the ossicular chain, for example, the manubrium, body of malleus, body of incus, short process of incus, long process of incus, stapes head or stapes footplate can be reached with the free active end of the hearing aid transducer, when coupled to the malleus, incus or short process of incus the naturally present connecting channel (aditus ad antrum) in the posterior wall of the auditory canal is used as the passage for the free active end between the mastoid antrum and middle ear, when coupled to the long process of incus, the stapes head or the stapes footplate, a hole made in the chorda-facial recess of the posterior bony wall of the auditory canal with a diameter of roughly 2 mm is used as the passage for the free active end of the hearing aid transducer, the positioning system described according to the invention is designed such that the surgeon intraoperatively has sufficiently unobstructed view of the active end of the hearing aid transducer even when using a microscope, the positioned hearing aid transducer after coupling to the ossicular chain can be fixed permanently and securely in the intraoperatively defined position by means of the clamp mechanism described according to the invention, the entire positioning system consists of biocompatible implant materials which are stable over the long term, all manipulations for attachment to the cranial bone, for positioning and for final fixing in situ can be done with a few auxiliary tools such as, for example, a screw driver and an Allen wrench, the system is optimized such that it absorbs the reaction of the vibrating piezotransducer, but does not convey it as a vibratory stimulus to the cranial bone, and thus reverse bone conduction transport of the auditory signal to the microphone located in the vicinity is suppressed, the positioning system is designed such that all its controls, even after placement in the implantation site, point away from the body of the patient, and thus, can be manually operated by the surgeon without difficulty, removal of any middle ear structures and surgical removal of ossicles are unnecessary, the external auditory canal in its entirety and most of the middle ear spaces remain free of implant components.

The described features and other features of the invention are detailed below with reference to the attached drawings.

DETAILED DESCRIPTION OF THE PREFERRED EMBODIMENTS

Figure 1:
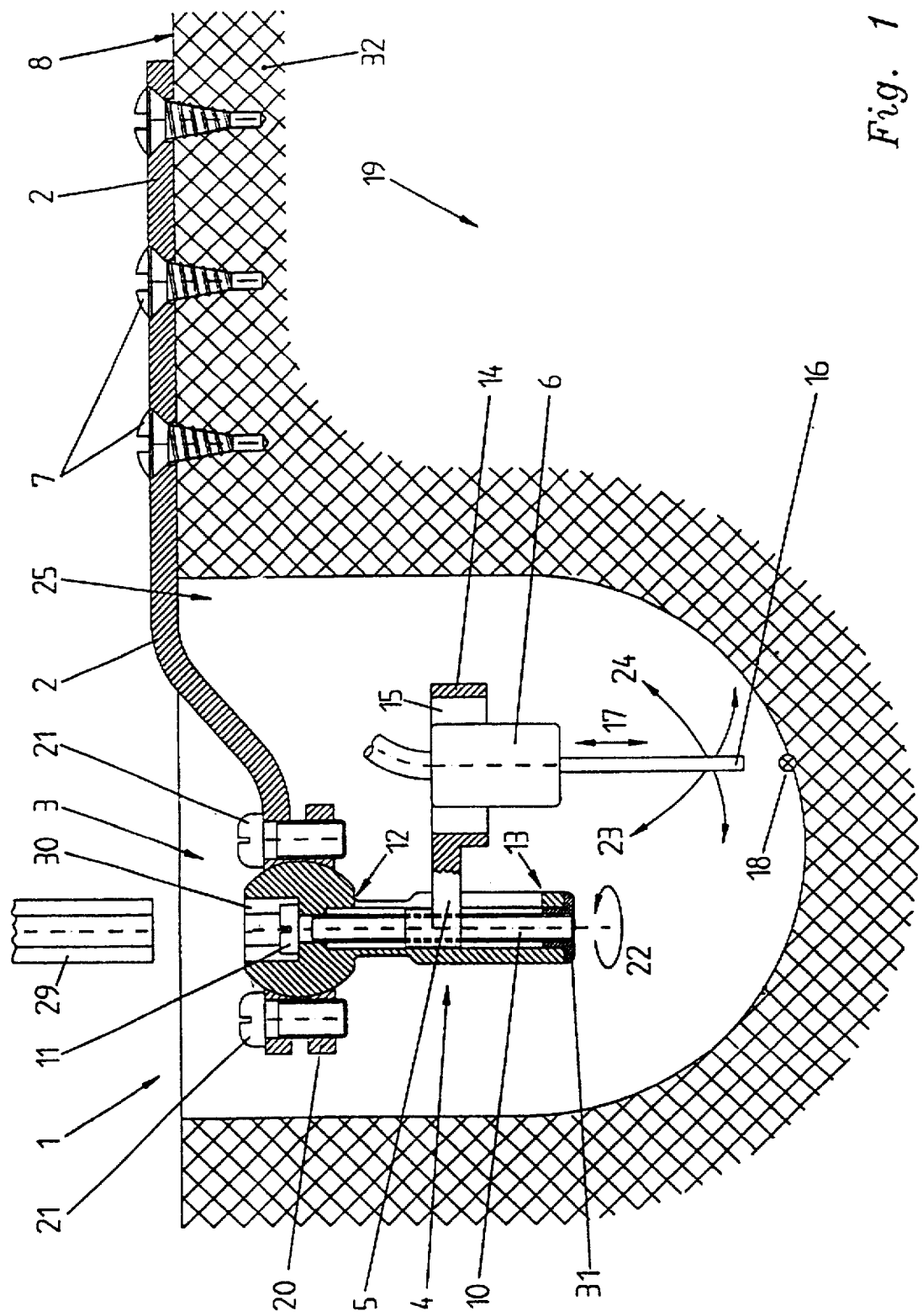
FIG. 1 shows a sectional view through the implantable positioning system according to the invention and through the cranial bone and the mastoid antrum.
Figure 2:
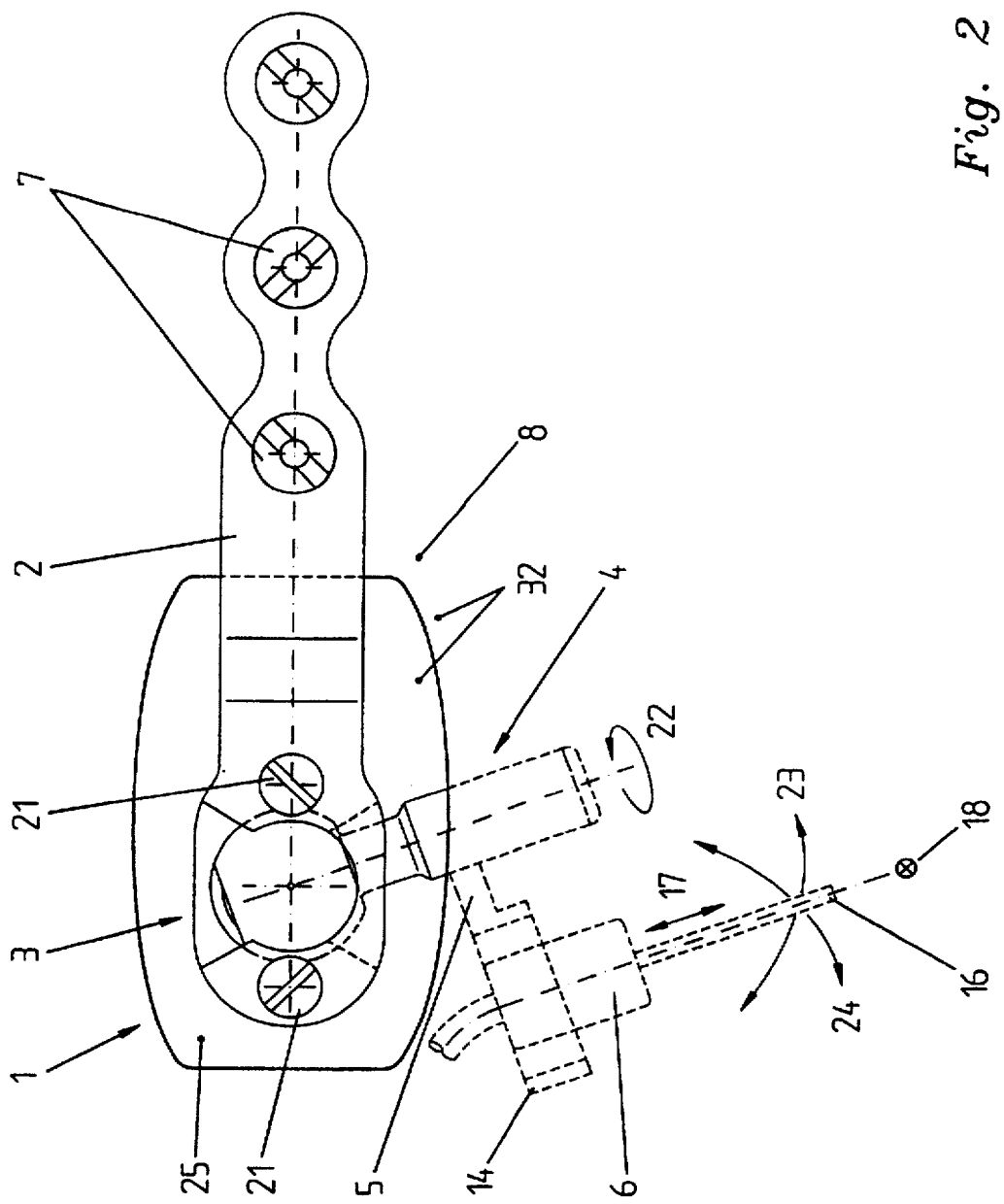
FIG. 2 shows a schematic overhead view of the positioning system shown in FIG. 1.

Implantable positioning and fixing system 1 shown in FIGS. 1 and 2 has head plate 2 which is suitable for bone anchoring, clampable ball-and-socket joint 3, linear axle 4 fixed stationary to it, and carriage 5 guided along the linear axle for accommodating any implantable actuator or sensor means 6, which as noted initially above, is shortened herein to "implantable means".

Head plate 2 of overall system 1 can be screwed tight to bone surfaces 8, for example, cranial bone 32, by means of suitable bone screws 7. The free end of the head plate is offset in stages, and attached to it are the clampable ball-and-socket joint 3, linear axle 4 and implantable means 6 which is held in carriage 5.

Projection of positioning system 1 above the level of bone surface 8 is prevented by the stepped offset of the free end of head plate 2 after the latter is screwed onto bone surface 8 of skull 32 and after the associated insertion of the primary system components (i.e., the head plate 3, linear axle 4, carriage 5 and implantable means 6) into suitable body cavity 25.

The ball of clampable ball-and-socket joint 3 is centered and held in suitable ball depressions between head plate 2 and counterplate 20. Two plates 2 and 20 can be moved together or apart by one or more attachment screws 21.

By tightening attachment screws 21, the ball is pressed into the ball depressions of two plates 2, 20. The instantaneous position of ball-and-socket joint 3 and of the linear axle 4 as well as implantable means 6 attached to it is thus easily fixed in space.

By loosening attachment screws 21, the ball-and-socket joint can be freely swiveled in its ball seat in all three degrees of rotational freedom 22, 23, 24. In this case, complete 360° rotation (arrow 22) around the longitudinal axis of linear axle 4 is possible. The swivel angles along the two other degrees of rotational freedom 23 and 24 are each roughly 160°.

To position ball-and-socket joint 3, attachment screws 21 are loosened only to such a degree that the ball is still held by friction forces in the ball depressions of head plate 2 and counterplate 20. A change in the instantaneous position of implantable means 6 by tilting due to the active forces of gravitation is thus prevented.

On the side of the ball which points away from the body, therefore toward the surgeon, cavity 30 is made into which suitable auxiliary tool 29, for example, an Allen wrench, can be inserted by form-fit. Thus, the ball of ball-and-socket joint 3 can be turned in the ball seat in all three degrees of rotational freedom 22, 23, and 24.

Linear axle 4 has a linear guide 9 in which the carriage 5 is guided without play. To move carriage 5, there is a threaded spindle 10 which has an operating end 11 which is fixed to the threaded spindle 10. The thread pitch of threaded spindle 10 is designed to be self-locking, so that carriage 5 cannot move independently in linear guide 9 due to the forces of gravitation, for example.

By form-fitted insertion of a suitable auxiliary tool into cavities of operating end 11 and by manual rotation of the operating end 11 itself, axial displacement of the carriage 5 in the guide 9 of linear axle 4 is produced according to the direction of the thread and the selected pitch of threaded spindle 10. On the top end of the linear axle 4, the axial path of the carriage 5 is limited by the ball of clampable ball-and-socket joint 3. On the lower end of the linear axle, an end stop 13 is used as a path limiter. As an alternative to the end stop 13, a cover plate 31 which can turn, which is fixed to threaded spindle 10, and which limits the axial path of the carriage can be used. Carriage 5 can thus move continuously along the linear axle 4 between end stops 12 and 13 or 31, and as a result of the self-locking of threaded drive 10, 11, it maintains its instantaneous position. The length of the path of movement of the carriage 5 on linear axle 4, in one preferred embodiment, is 5 to 10 mm. In FIGS. 1 and 2, the carriage is shown in an intermediate position between the two end stops.

Carriage 5 has a receiver 14 into which the desired implantable means 6 can be inserted without play. If mechanical decoupling or elastic bearing between positioning system 1 and implantable means 6 fixed in receiver 14 is necessary, an elastic or spring-elastic intermediate piece 15 can be inserted between the receiver 14 and the implantable means 6.

Free active end 16 of implantable means 6, inserted in receiver 14 of carriage 5, can thus be positioned by turning the operating end 11 of the threaded spindle 10 parallel to linear guide 9 in axial direction 17 with reference to destination 18 in human body 19.

When the ball-and-socket joint 3 is released, the entire linear axle 4 can be turned around the center of the ball which is supported stationary between head plate 2 and counterplate 20 in all three degrees of rotational freedom 22, 23, and 24. In conjunction with the axial degree of freedom 17 of linear axle 4, there are thus four degrees of freedom available in space for positioning of the implantable means.

FIG. 2 shows that, with positioning system 1, destinations 18 which are located under the skull cap can be reached by the free active end 16 of the implantable means 6 attached in the system.

Figure 3:
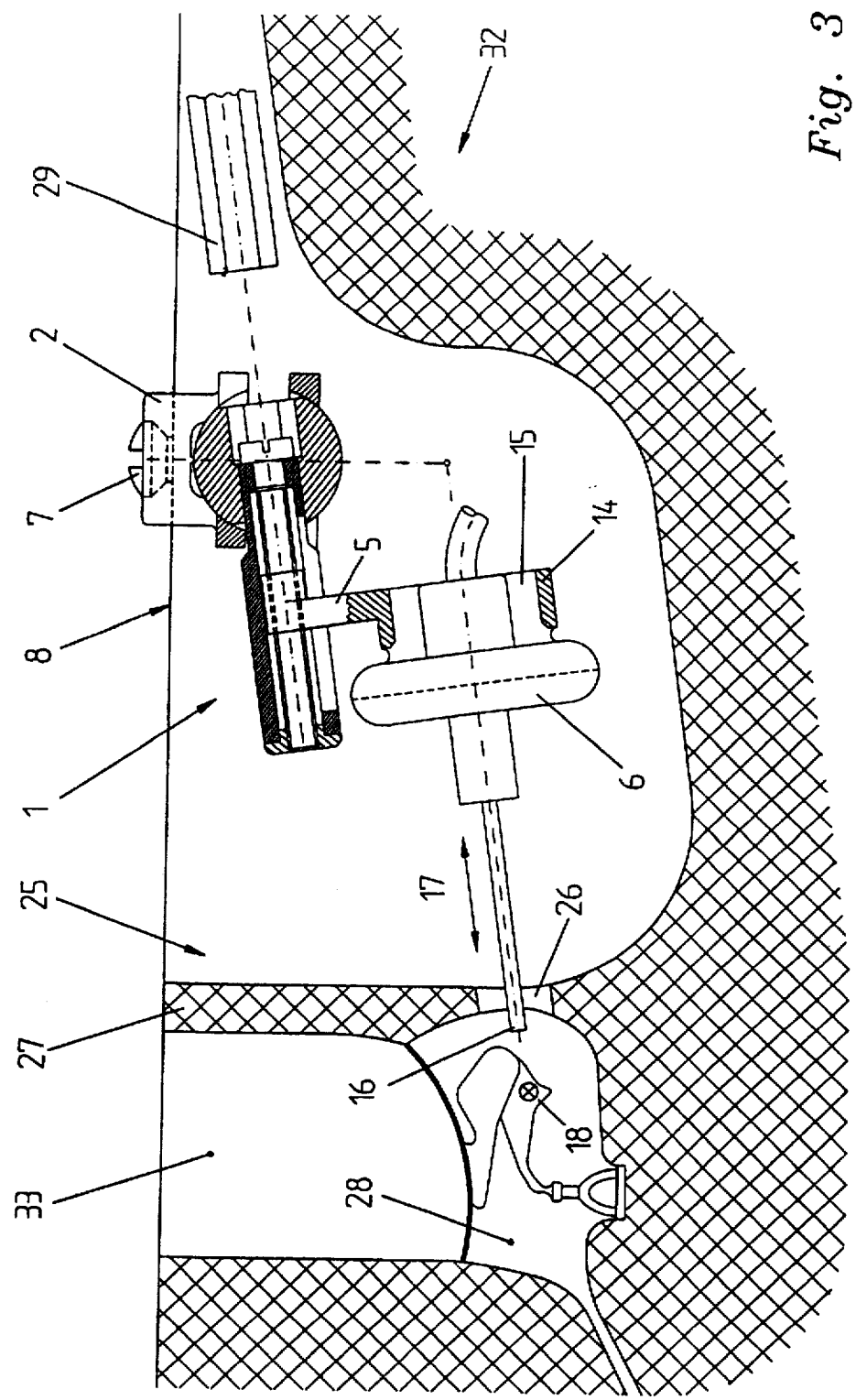
FIG. 3 shows a sectional view of the mastoid antrum and the middle ear as well as the positioning system according to the invention, in which the head plate is fixed on the surface of the skull, the linear axle is swiveled to the maximum degree around the ball center, and the free active end of a hearing aid actuator points through the anterior auditory canal wall to the destination in the middle ear.
Figure 4:
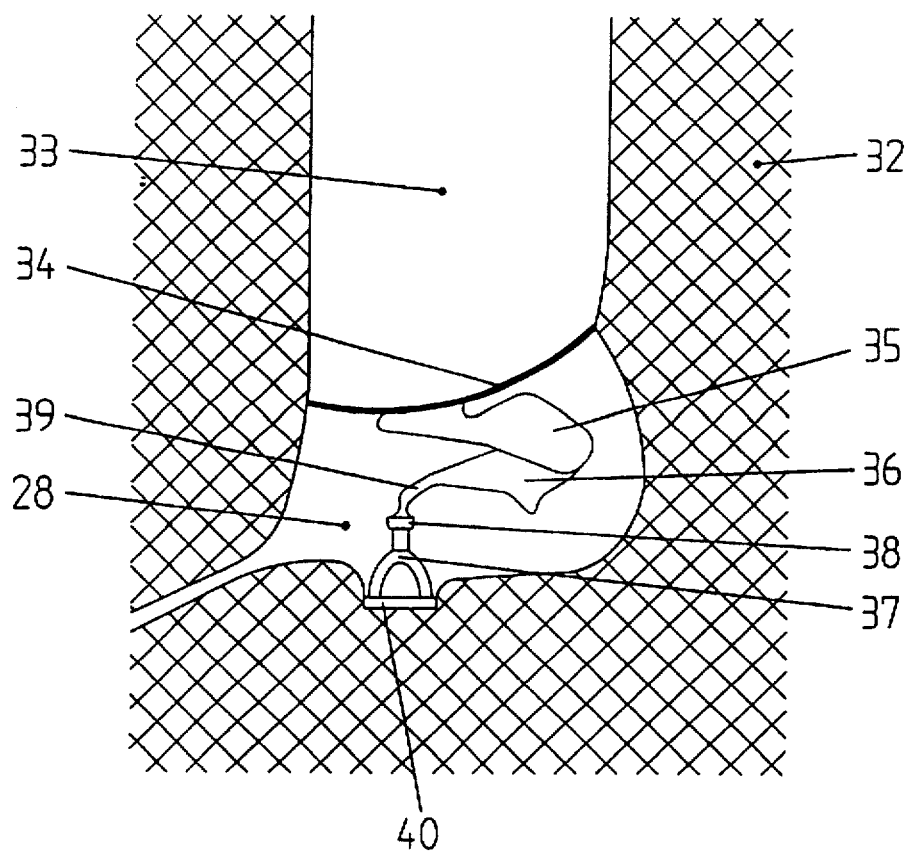
FIG. 4 shows a schematic cross section of the middle ear with possible coupling points for the free active end of the hearing aid actuator.

FIG. 3 shows one preferred application of the positioning and fixing system. FIG. 4 shows the possible coupling points in the middle ear 28 which is separated from the external auditory canal 33 by the eardrum 34. In this case, a hearing aid transducer which is suitable for vibratory stimulation of the ossicular chain serves as the implantable means 6 and is held in receiver 14 of carriage 5. The hearing aid transducer is a component of a partially or completely implantable hearing aid. In this preferred application of the invention, the destination 18 on the body is a point on the ossicular chain, i.e., the malleus 35, incus 36 or stapes 37 (FIG. 4).

According to this application of the invention, the body opening 25, into which positioning system 1 can be implanted, positioned and fixed intraoperatively with auxiliary tools, is the mastoid antrum 25 located in the skull bone 32. Head plate 2 is screwed onto surface 8 of skull bone 32 in an area which borders the mastoid antrum. The free active end 16 of the hearing aid transducer forming implantable means 6 extends through the bone opening 26 of rear auditory passage wall 27 into the middle ear 28. Depending on the situation of the mastoid antrum 25, anterior auditory canal wall 27 and middle ear 28 (found anatomically beforehand), the surgeon selects a destination 18 on the ossicular chain (malleus 35, incus 36, stapes 37) which is best suited for the case.

For coupling to the body of the incus 36, a naturally present canal in rear auditory canal wall 27, the aditus ad antrum, can be used as a bone opening 26 for the free active end 16 of hearing aid transducer 6. For coupling to long process of incus 39, processus lenticularis 38, and to structures of stapes 37, for example, the footplate 40 of the stapes, a suitable bone opening 26 must be bored in the rear auditory passage wall 27. This opening is made in the chordafacialis angle and has a diameter of roughly 2 mm.

Coupling of the free active end 16 of the hearing aid transducer of implantable means 6 to the auditory ossicles of the middle ear (malleus, incus, stapes) and to structures of the inner ear and the vestibular organ is possible by suitable measures.

Suitable actuators or sensors for use as the implantable means 6, for application of positioning system 1 are, among others, active electromechanical hearing aid transducers for electromechanical stimulation of the ossicular chain, excitor coils for the electromagnetic stimulation of permanent magnets affixed to the ossicular chain, optical fibers for guiding surgical laser light (for example, for cutting, drilling, coagulating or excising tissue or bone structures), optical fibers for guiding laser instrumentation light baser Doppler vibrometry), flexible miniature endoscopes for inspection of any skull regions, probe microphones and small sound sources for intraoperative audiometry (determination of the auditory threshold, derivation of otacoustic emission) and electrodes for deriving electrocochleographic body potentials (for example, sum action potential or microphone potential) or for electrostimulation within the framework of preoperative hearing tests before implantation of cochlear implants (promontorial tests).

While various embodiments in accordance with the present invention have been described and a preferred embodiment shown, it is understood that the invention is not limited thereto, and is susceptible to numerous changes and modifications as known to those skilled in the art. Therefore, this invention is not limited to the details shown and described herein, and includes all such changes and modifications as are encompassed by the scope of the appended claims.

We claim:

1. A permanently implantable, positioning and fixing system for positioning and subsequent fixing of an implantable device relative to a human body, comprising:

a fixing member constructed for affixing to the human body:

a ball-and-socket joint having a socket which is attached to said fixing member and a ball having an auxiliary tool receiver by which the ball is positionable relative to the socket with an auxiliary tool;

a clamp mechanism cooperating with said ball-and-socket joint for selectively fixing said ball relative to said socket;

a linear guide rail which is fixed to the ball of the ball-and-socket joint;

carriage which is guided in a guide of said guide rail for linear movement relative to said guide rail;

a linear drive means for displacing said carriage relative to said guide rail; and a receiver for receiving said implantable device, said receiver being attached to the carriage.

2. Positioning system according to claim 1, wherein the linear drive means is self-locking.

3. Positioning system according to claim 1, wherein said linear drive comprises a threaded spindle; and wherein the positioning system provides four degrees of freedom of positional adjustment for a free active end of a selected implantable device attached to the receiver, one of said four axial degrees of freedom being an axial degree of freedom provided by the threaded spindle and three of said four degrees of freedom being provided by the ball-and-socket joint.

4. Positioning system according to claim 3, wherein the ball-and-socket joint is provided with means for fictionally maintaining instantaneous positions thereof in said three degrees of rotational freedom when said clamping mechanism is released.

5. Positioning system according to claim 1, wherein said linear drive means includes a threaded spindle which is mounted for rotation relative to said guide rail and which is in threaded engagement with said carriage for positioning said carriage by rotating said threaded spindle.

6. Positioning system according to claim 5, wherein said threaded spindle is provided, at the end thereof close to said ball, with means for receiving an operating tool for rotating said spindle.

7. Positioning system according to claim 1, wherein said clamp mechanism comprises a pair of spaced plates which define the socket of said ball-and-socket joint and between which the ball of said ball-and-socked joint is mounted, and clamping screws in engagement with said plates for adjusting clamping pressure applied by said plates to the ball of said ball-and-socket joint.

8. Positioning system according to claim 1, wherein the ball of said ball-and-socket joint is provided, at a side thereof averted from said guide rail, with a receiving opening for receiving an end of said auxiliary tool for positioning said ball relative to said socket of said ball-and-socket joint when said clamp mechanism is released.

9. Positioning system according to claim 1, wherein said fixing member comprises a head plate provided with openings for inserting bone screws for attaching the positioning system to a surface of a skull bone.

10. Positioning system according to claim 1, wherein the positioning system is made of implantable metals.

11. Positioning system according to claim 10, wherein said implantable metals are selected from the group consisting of pure titanium, implantable alloys of titanium and implantable steels.

12. Positioning system according to claim 1, wherein said linear guide rail includes a pair of spaced end stops; and wherein said carriage is guided in said guide of said guide rail for linear movement between said end stops.

\* \* \* \* \*